United States Patent
Hincapie Ordonez et al.

(10) Patent No.: US 9,254,389 B2
(45) Date of Patent: Feb. 9, 2016

(54) ELECTRICAL INHIBITION OF THE PHRENIC NERVE DURING CARDIAC PACING

(71) Applicant: Cardiac Pacemakers, Inc., St. Paul, MN (US)

(72) Inventors: Juan Gabriel Hincapie Ordonez, Maple Grove, MN (US); Holly Rockweiler, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 102 days.

(21) Appl. No.: 14/094,254

(22) Filed: Dec. 2, 2013

(65) Prior Publication Data

US 2014/0088661 A1 Mar. 27, 2014

Related U.S. Application Data

(62) Division of application No. 12/963,399, filed on Dec. 8, 2010, now Pat. No. 8,620,428.

(60) Provisional application No. 61/287,308, filed on Dec. 17, 2009.

(51) Int. Cl.
*A61N 1/365* (2006.01)
*A61N 1/362* (2006.01)
*A61N 1/37* (2006.01)
*A61N 1/36* (2006.01)
(Continued)

(52) U.S. Cl.
CPC .............. *A61N 1/365* (2013.01); *A61B 5/4041* (2013.01); *A61N 1/3627* (2013.01); *A61N 1/36167* (2013.01); *A61N 1/3712* (2013.01); *A61B 5/0205* (2013.01); *A61B 5/04001* (2013.01); *A61B 5/0809* (2013.01); *A61B 5/0816* (2013.01); *A61B 5/113* (2013.01); *A61B 5/1107* (2013.01); *A61N 1/3601* (2013.01)

(58) Field of Classification Search
CPC ... A61N 1/3627; A61N 1/371; A61N 1/3601; A61N 1/36167; A61N 1/365; A61B 5/04001; A61B 5/0205; A61B 5/1107; A61B 5/0816; A61B 5/0809; A61B 5/4052
See application file for complete search history.

(56) References Cited

U.S. PATENT DOCUMENTS

| 4,541,417 A | 9/1985 | Krikorian |
|---|---|---|
| 5,861,022 A | 1/1999 | Hipskind |

(Continued)

FOREIGN PATENT DOCUMENTS

| WO | WO-0141868 A1 | 6/2001 |
| WO | WO-2009058258 A1 | 5/2009 |
| WO | WO-2011084325 A1 | 7/2011 |

OTHER PUBLICATIONS

"U.S. Appl. No. 12/963,399, Response filed Apr. 9, 2013 to Non Final Office Action mailed Jan. 11, 2013", 17 pgs.

(Continued)

*Primary Examiner* — Catherine Voorhees
(74) *Attorney, Agent, or Firm* — Schwegman Lundberg & Woessner, P.A.

(57) ABSTRACT

According to various method embodiments for pacing a heart and avoiding unwanted stimulation of a phrenic nerve during cardiac pacing, a desired pacing time for delivering a cardiac pace is determined, and a desired nerve traffic inhibition time to inhibit nerve traffic in the phrenic nerve is determined using the desired pace time. The cardiac pace is delivered at the desired pacing time and nerve traffic in the phrenic nerve is inhibited at the desired nerve traffic inhibition time.

20 Claims, 14 Drawing Sheets

(51) Int. Cl.
  *A61B 5/0205* (2006.01)
  *A61B 5/04* (2006.01)
  *A61B 5/08* (2006.01)
  *A61B 5/00* (2006.01)
  *A61B 5/11* (2006.01)
  *A61B 5/113* (2006.01)

(56) References Cited

U.S. PATENT DOCUMENTS

| | | | |
|---|---|---|---|
| 6,152,953 | A | 11/2000 | Hipskind |
| 6,415,183 | B1 | 7/2002 | Scheiner et al. |
| 6,463,327 | B1 | 10/2002 | Lurie et al. |
| 6,587,726 | B2 | 7/2003 | Lurie et al. |
| 6,735,471 | B2 | 5/2004 | Hill et al. |
| 6,772,008 | B2 | 8/2004 | Zhu et al. |
| 6,928,320 | B2 | 8/2005 | King |
| 7,082,331 | B1 | 7/2006 | Park et al. |
| 7,094,207 | B1 | 8/2006 | Koh |
| 7,277,757 | B2 | 10/2007 | Casavant et al. |
| 7,299,093 | B2 | 11/2007 | Zhu et al. |
| 7,340,302 | B1 | 3/2008 | Falkenberg et al. |
| 7,392,086 | B2 | 6/2008 | Sathaye |
| 7,430,447 | B2 | 9/2008 | Min et al. |
| 7,454,250 | B1 | 11/2008 | Bjorling et al. |
| 2003/0065365 | A1 | 4/2003 | Zhu et al. |
| 2005/0021102 | A1 | 1/2005 | Ignagni et al. |
| 2006/0122661 | A1 | 6/2006 | Mandell |
| 2006/0217772 | A1 | 9/2006 | Libbus et al. |
| 2006/0241711 | A1 | 10/2006 | Sathaye |
| 2006/0282121 | A1 | 12/2006 | Payne et al. |
| 2006/0293609 | A1 | 12/2006 | Stahmann et al. |
| 2007/0156199 | A1 | 7/2007 | Koh et al. |
| 2007/0265611 | A1 | 11/2007 | Ignagni et al. |
| 2008/0077186 | A1 | 3/2008 | Thompson et al. |
| 2008/0243196 | A1 | 10/2008 | Libbus et al. |
| 2010/0036451 | A1 | 2/2010 | Hoffer |
| 2010/0305638 | A1 | 12/2010 | McCabe et al. |
| 2010/0305647 | A1 | 12/2010 | Mccabe et al. |
| 2011/0152956 | A1 | 6/2011 | Ordonez et al. |

OTHER PUBLICATIONS

"U.S. Appl. No. 12/963,399, Response filed Aug. 5, 2013 to Final Office Action mailed Jun. 6, 2013", 13 pgs.
"U.S. Appl. No. 12/963,399, Final Office Action mailed Jun. 6, 2013", 15 pgs.
"U.S. Appl. No. 12/963,399, Non Final Office Action mailed Jan. 1, 2013", 19 pgs.
"U.S. Appl. No. 12/963,399, Notice of Allowance mailed Aug. 23, 2013", 6 pgs.
"International Application Serial No. PCT/US2010/059472, International Preliminary Report on Patentability mailed Jun. 28, 2012", 8 pgs.
"International Application Serial No. PCT/US2010/059472, International Search Report mailed Apr. 11, 2011", 6 pgs.
"International Application Serial No. PCT/US2010/059472, Written Opinion mailed Apr. 11, 2011", 7 pgs.
"Japanese Application Serial No. 2012-544625, Office Action mailed Sep. 26, 2013", with English Translation, 4 pgs.
Ackermann, D M, et al., "Effect of bipolar cuff electrode design on block thresholds in high-frequency electrical neural conduction block.", IEEE Trans Neural Syst Rehabil Eng., 17(5), (Oct. 2009), 469-77.
Ackermann, D., et al., "Electrode design for high frequency block: effect of bipolar separation on block thresholds and the onset response", Annual International Conference of the IEEE Engineering in Medicine and Biology Society, 2009. EMBC 2009., 654-7.
Albertsen, A. E, et al., "Left ventricular lead performance in cardiac resynchronization therapy: impact of lead localization and complications.", Pacing Clin Electrophysiol., 28(6), (Jun. 2005), 483-8.
Alonso, C., et al., "Six year experience of transvenous left ventricular lead implantation for permanent biventricular pacing in patients with advanced heart failure: technical aspects.", Heart, 86(4), (Oct. 2001), 405-10.
Azizi, M., et al., "Experience with coronary sinus lead implantations for cardiac resynchronization therapy in 244 patients.", Herzschrittmacherther Elektrophysiol., 17(1), (Mar. 2006), 13-8.
Bhadra, N, et al., "Direct current electrical conduction block of peripheral nerve.", IEEE Trans Neural Syst Rehabil Eng., 12(3), (Sep. 2004), 313-24.
Bhadra, N, et al., "High frequency electrical conduction block of the pudendal nerve.", J Neural Eng., 3(2), (Jun. 2006), 180-7.
Bhadra, N, et al., "High-frequency nerve conduction block.", Conf Proc IEEE Eng Med Biol Soc., 7, (2004), 4729-32.
Bhadra, N, et al., "Implementation of an implantable joint-angle transducer.", J Rehabil Res Dev., 39(3), (May-Jun. 2002), 411-22.
Bhadra, N, et al., "Reduction of the onset response in high frequency nerve block with amplitude ramps from non-zero amplitudes.", Annual International Conference of the IEEE Engineering in Medicine and Biology Society, 2009. EMBC 2009., 650-653.
Bhadra, N, et al., "Simulation of high-frequency sinusoidal electrical block of mammalian myelinated axons.", J Comput Neurosci., 22(3), (Jun. 2007), 313-26.
Bhadra, N., et al., "Direct current electrical conduction block peripheral nerve", IEEE Transactions on Neural Systems and Rehabilitaion Engineering, 12(3), (Sep. 2004), 313-324.
Bhadra, N., et al., "High-frequency electrical conduction block of mammalian peripheral motor nerve", Muscle Nerve, 32(6), (Dec. 2005), 782-90.
Biffi, M., et al., "Phrenic Stimulation: A Challenge for Cardiac Resynchronization Therapy", Circulation: Arrhythmia and Electrophysiology, 2, (2009), 402-410.
Burke, M. C, et al., "Implications and outcome of permanent coronary sinus lead extraction and reimplantation", J Cardiovasc Electrophysiol.,16(8), (Aug. 2005), 830-7.
Ellery, S., et al., "A new endocardial "over-the-wire" or stylet-driven left ventricular lead: first clinical experience.", Pacing Clin Electrophsiol., 28 Suppl 1, (Jan. 2005), S31-5.
Foldes, E. L, et al., "Counted cycles method to quantify the onset response in high-frequency peripheral nerve block.", Annual International Conference of the IEEE Engineering in Medicine and Biology Society, 2009, EMBC 2009., 614-617.
Grill, W. M, et al., "Stimulus waveforms for selective neural stimulation", IEEE Engineering in Medicine and Biology Magazine, 14(4), (1995), 375-385.
Gurevitz, O., et al., "Programmable multiple pacing configurations help to overcome high left ventricular pacing thresholds and avoid phrenic nerve stimulation.", Pacing Clin Electrophysiol., 28(12), (Dec. 2005), 1255-9.
Hart, R, et al., "Design and Testing of an Advanced Implantable Neuroprosthesis With Myoelectric Control.", IEEE Trans Neural Syst Rehabil Eng., [Epub ahead of print], (Sep. 27, 2010).
Kilgore, K L, et al., "Combined direct current and high frequency nerve block for elimination of the onset response.", Annual International Conference of the IEEE Engineering in Medicine and Biology Society, 2009. EMBC 2009., 197-199.
Kilgore, K. L, et al., "High frequency mammalian nerve conduction block: simulations and experiments.", 28th Annual International Conference of the IEEE Engineering in Medicine and Biology Society, 2006. EMBS '06., (2006), 4971-4974.
Kilgore, K. L, et al., "Nerve conduction block utilising high-frequency alternating current.", Med Biol Eng Comput., 42(3), (May 2004), 394-406.
Luo, Y. M, et al., "Diaphragm electromyography using an oesophageal catheter: current concepts.", Clin Sci (Lond), 115(8), (Oct. 2008), 233-44.
Miles, J. D, et al., "Effects of ramped amplitude waveforms on the onset response of high-frequency mammalian nerve block.", J Neural Eng., 4(4), (Dec. 2007), 390-8.
Purerfellner, H., et al., "Transvenous left ventricular lead implantation with the Easytrak lead system: the European experience", Am J Cardiol., 86(9A), (Nov. 2, 2000), 157K-164K.
Schuchert, A., et al., "Two-Year Performance of a Preshaped Lead for Left Ventricular Stimulation", Pacing and Clinical Electrophysiology, 27(12), (2004), 1610-1614.

ELECTRICAL INHIBITION OF THE PHRENIC NERVE DURING CARDIAC PACING

CLAIM OF PRIORITY

This application is a divisional of U.S. application Ser. No. 12/963,399, filed Dec. 8, 2010, now issued as U.S. Pat. No. 8,620,428, which claims the benefit of priority under 35 U.S.C. §119(e) of U.S. Provisional Patent Application Ser. No. 61/287,308, filed on Dec. 17, 2009, which is herein incorporated by reference in its entirety.

TECHNICAL FIELD

This application related generally to medical devices and, more particularly, to systems, devices and methods for electrically inhibiting the phrenic nerve.

BACKGROUND

When the heart is paced in the left ventricle (LV), there may be unwanted stimulation of the phrenic nerve that causes contraction of the diaphragm. The left phrenic nerve descends on the pericardium to penetrate the left part of the diaphragm, and in most people, the left phrenic nerve runs close to the lateral vein. In the clinic, the pacing configuration or the stimulation parameters may be modified in an effort to avoid phrenic nerve stimulation. Examples of pacing configurations include LV bipolar, LV to can, LV to RV (right ventricle) also referred to as "extended bipolar"; and examples of stimulation parameters include the amplitude (e.g. voltage) and pulse width. The anatomic location of the phrenic nerve varies within patients. Additionally, the veins are not always in the same location with respect to the ventricle and the nearby passing nerve. Also, the selected vein in which to place the lead may vary.

Unintended phrenic nerve activation (an unintended action potential propagated in the phrenic nerve) is a well-known consequence of left ventricular pacing. The unintended phrenic nerve activation may cause the diaphragm to undesirably contract. Unintended phrenic nerve activation may feel like hiccups to the patient. Unintended phrenic nerve activation can occur when the electric field of the LV pacing lead is proximate to the left phrenic nerve and is at a stimulation output that is strong enough to capture the nerve. As a consequence, unintended capture of the phrenic nerve may require modification of the strategy for implanting the pacing lead. For example, the LV pacing electrodes may not be positioned in a preferred position to capture the LV for a pacing therapy such as CRT, or the clinician may decide not to implant an LV pacing electrode but rather rely on other pacing algorithms that do not pace the LV. A special office visit after implant may be necessary or desirable to reprogram the device to avoid phrenic nerve stimulation. Further, although phrenic nerve stimulation is commonly assessed at implant, unintended phrenic nerve activation caused by phrenic nerve capture during pacing can appear post-implant for a variety of reasons such as reverse remodeling of the heart, lead microdislodgement, changes in posture, and the like.

SUMMARY

Various system embodiments for pacing a heart and avoiding unwanted stimulation of a phrenic nerve include a cardiac pulse generator, a nerve traffic inhibitor, a cardiac activity sensor, and a controller. The cardiac pulse generator is configured to generate cardiac paces to pace the heart. The nerve traffic inhibitor is configured to generate an electrical signal to inhibit nerve traffic in the phrenic nerve. The cardiac activity sensor is configured to sense cardiac activity. The controller is operably connected to the cardiac pulse generator, the nerve traffic inhibitor, and the cardiac activity sensor. The controller includes a cardiac pacing timer and a nerve traffic inhibition timer. The controller is configured to use sensed cardiac activity and the cardiac pacing timer to determine a desired pace time for a cardiac pace. The controller is configured to use the desired pace time and a nerve traffic inhibition timer to control the nerve traffic inhibitor to inhibit nerve traffic in the phrenic nerve at a desired inhibition time with respect to the desired pace time to prevent the cardiac pace from stimulating the phrenic nerve.

According to various method embodiments for avoiding unwanted stimulation of phrenic nerve during cardiac pacing, a desired pace time for delivering a cardiac pace is received, and a desired nerve traffic inhibition time to inhibit nerve traffic in the phrenic nerve is determined using the desired pace time. Nerve traffic in the phrenic nerve is inhibited at the desired nerve traffic inhibition time.

According to various method embodiments for pacing a heart and avoiding unwanted stimulation of a phrenic nerve during cardiac pacing, a desired pacing time for delivering a cardiac pace is determined, and a desired nerve traffic inhibition time to inhibit nerve traffic in the phrenic nerve is determined using the desired pace time. The cardiac pace is delivered at the desired pacing time and nerve traffic in the phrenic nerve is inhibited at the desired nerve traffic inhibition time.

This Summary is an overview of some of the teachings of the present application and not intended to be an exclusive or exhaustive treatment of the present subject matter. Further details about the present subject matter are found in the detailed description and appended claims. The scope of the present invention is defined by the appended claims and their equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Figure 1A:
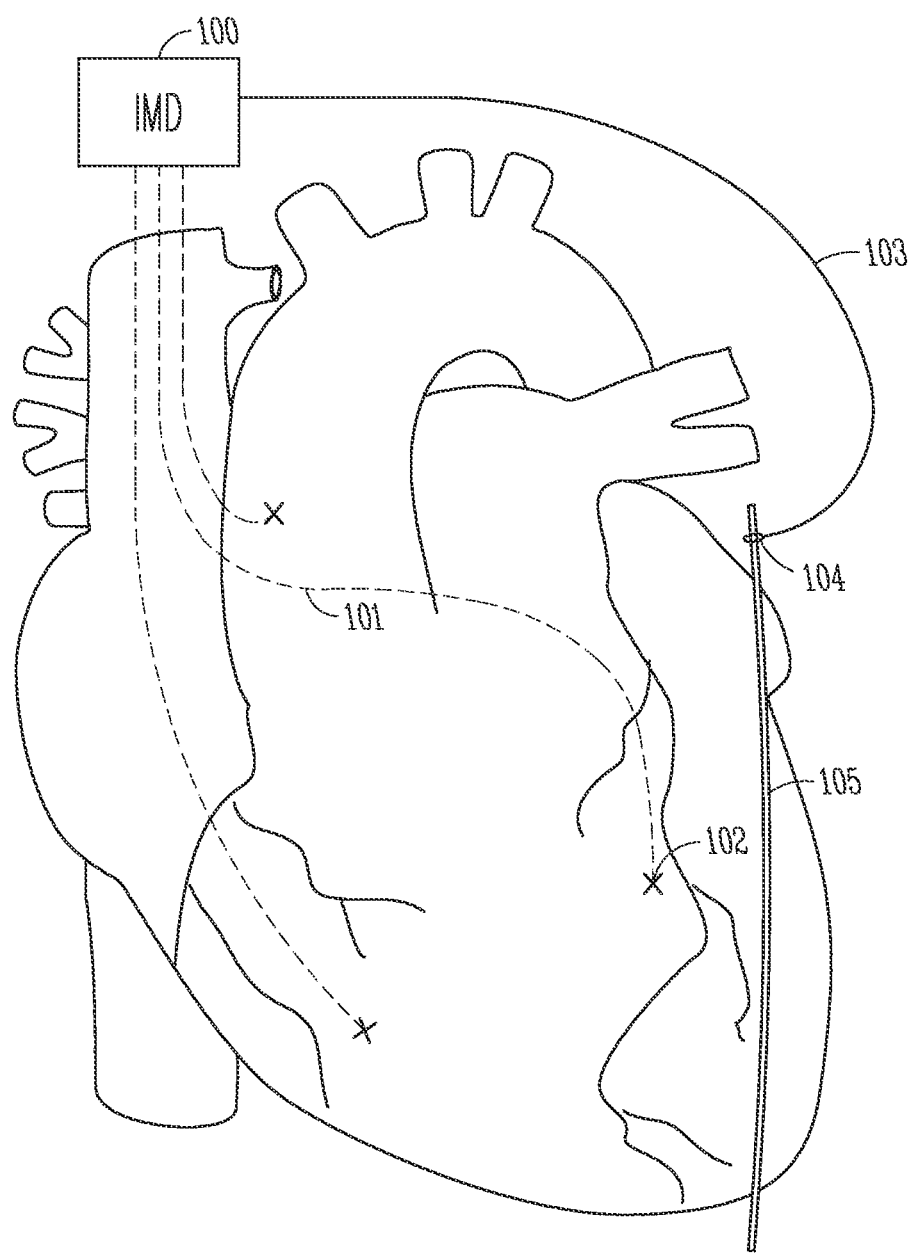
FIGS. 1A-1E illustrate various implantable device embodiments configured to stimulate the left ventricle and configured to inhibit phrenic nerve activity.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an," "one," or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

A myocardial stimulation therapy provides a cardiac therapy using electrical stimulation of the myocardium. Some examples of myocardial stimulation therapies are provided below. A pacemaker is a device which paces the heart with timed pacing pulses, most commonly for the treatment of bradycardia where the ventricular rate is too slow. If functioning properly, the pacemaker makes up for the heart's inability to pace itself at an appropriate rhythm in order to meet metabolic demand by enforcing a minimum heart rate. Implantable devices have also been developed that affect the manner and degree to which the heart chambers contract during a cardiac cycle in order to promote the efficient pumping of blood. The heart pumps more effectively when the chambers contract in a coordinated manner, a result normally provided by the specialized conduction pathways in both the atria and the ventricles that enable the rapid conduction of excitation (i.e., depolarization) throughout the myocardium. These pathways conduct excitatory impulses from the sino-atrial node to the atrial myocardium, to the atrio-ventricular node, and thence to the ventricular myocardium to result in a coordinated contraction of both atria and both ventricles. This both synchronizes the contractions of the muscle fibers of each chamber and synchronizes the contraction of each atrium or ventricle with the contralateral atrium or ventricle. Without the synchronization afforded by the normally functioning specialized conduction pathways, the heart's pumping efficiency is greatly diminished. Pathology of these conduction pathways and other inter-ventricular or intra-ventricular conduction deficits can be a causative factor in heart failure, which refers to a clinical syndrome in which an abnormality of cardiac function causes cardiac output to fall below a level adequate to meet the metabolic demand of peripheral tissues. In order to treat these problems, implantable cardiac devices have been developed that provide appropriately timed electrical stimulation to one or more heart chambers in an attempt to improve the coordination of atrial and/or ventricular contractions, termed cardiac resynchronization therapy (CRT). Ventricular resynchronization is useful in treating heart failure because, although not directly inotropic, resynchronization can result in a more coordinated contraction of the ventricles with improved pumping efficiency and increased cardiac output. A CRT example applies stimulation pulses to both ventricles, either simultaneously or separated by a specified biventricular offset interval, and after a specified atrio-ventricular delay interval with respect to the detection of an intrinsic atrial contraction or delivery of an atrial pace.

CRT can be beneficial in reducing the deleterious ventricular remodeling which can occur in post-MI and heart failure patients, which appears to occur as a result of changes in the distribution of wall stress experienced by the ventricles during the cardiac pumping cycle when CRT is applied. The degree to which a heart muscle fiber is stretched before it contracts is termed the preload, and the maximum tension and velocity of shortening of a muscle fiber increases with increasing preload. When a myocardial region contracts late relative to other regions, the contraction of those opposing regions stretches the later contracting region and increases the preload. The degree of tension or stress on a heart muscle fiber as it contracts is termed the afterload. Because pressure within the ventricles rises rapidly from a diastolic to asystolic value as blood is pumped out into the aorta and pulmonary arteries, the part of the ventricle that first contracts due to an excitatory stimulation pulse does so against a lower afterload than does a part of the ventricle contracting later. Thus a myocardial region which contracts later than other regions is subjected to both an increased preload and afterload. This situation is created frequently by the ventricular conduction delays associated with heart failure and ventricular dysfunction due to an MI. The increased wall stress to the late-activating myocardial regions is most probably the trigger for ventricular remodeling. By pacing one or more sites in a ventricle near the infarcted region in a manner which may cause a more coordinated contraction, CRT provides pre-excitation of myocardial regions which would otherwise be activated later during systole and experience increased wall stress. The pre-excitation of the remodeled region relative to other regions unloads the region from mechanical stress and allows reversal or prevention of remodeling to occur.

Cardioversion, an electrical shock delivered to the heart synchronously with the QRS complex, and defibrillation, an electrical shock delivered without synchronization to the QRS complex, can be used to terminate most tachyarrhythmias. The electric shock terminates the tachyarrhythmia by simultaneously depolarizing the myocardium and rendering it refractory. A class of CRM devices known as an implantable cardioverter defibrillator (ICD) provides this kind of therapy by delivering a shock pulse to the heart when the device detects tachyarrhythmias. Another type of electrical therapy for tachycardia is anti-tachycardia pacing (ATP). In ventricular ATP, the ventricles are competitively paced with one or more pacing pulses in an effort to interrupt the reentrant circuit causing the tachycardia. Modern ICDs typically have ATP capability, and deliver ATP therapy or a shock pulse when a tachyarrhythmia is detected. ATP may be referred to as overdrive pacing. Other overdrive pacing therapies exist, such as intermittent pacing therapy (IPT), which may also be referred to as a conditioning therapy.

Both a right phrenic nerve and a left phrenic nerve pass near the heart and innervate the diaphragm below the heart. Various embodiments electrically inhibit or block nerve traffic in the left phrenic nerve during LV pacing so as to avoid unintended phrenic nerve activation caused by stimulation of the phrenic nerve, a common side effect of CRT. Pace-induced phrenic nerve activation may also be observed with other forms of pacing, particularly LV pacing, because of the close proximity of the LV pacing site to the left phrenic nerve. For example, various embodiments deliver a selective, nerve-blocking pulse waveform, that does not capture cardiac tissue, before and during pacing of the left ventricle. The inhibition pulse prevents phrenic nerve capture during the pacing pulse and thereby prevents activation of the diaphragm. Cardiac stimulation at other locations of the heart may result in unintended phrenic nerve activation in either the left or right phrenic nerve. The present subject matter is not limited to the inhibition of the left phrenic nerve during LV pacing, but may be implemented to appropriately address unintended phrenic nerve activation in either the left or right phrenic nerve caused by cardiac pacing.

The phrenic nerve blocking algorithms can be integrated with known sensing and pacing algorithms and circuitry. The PN blocking algorithm may be tailored for individual patients because of anatomical differences in the patient (e.g. the precise location of the phrenic nerve relative to the LV lead). Various embodiments determine the best electrode(s) from a plurality of electrodes for use in inhibiting phrenic nerve activity. A multi-polar lead presents more electrodes from which to block, and various embodiments are programmed with an algorithm to help a clinician choose the best electrode from which to block, and to verify that the blocking pulse is effective in alleviating the stimulation of phrenic nerve activity. According to some embodiments, the device is programmed to use sensors to detect unintended phrenic nerve activity or diaphragm contraction and to automatically choose electrodes from which to inhibit nerve activity.

Pace-induced phrenic nerve activation may be observed only when a patient is in a particular position (e.g. lying down) or activity level. The unintended phrenic nerve activation may not have been observed at the time that the stimulation device was implanted because of the patient position at the time of implantation, because of the effects of anesthesia, or because of other factors that are not present in a clinical setting. Some embodiments use a posture sensor to provide context. Some embodiments use an activity sensor to provide context. Some embodiments use a timer to determine a time of day to provide context. Whenever the context is sensed or otherwise identified or estimated (e.g. any time that the patient is lying down), the device may be programmed or otherwise configured to respond by initiating a procedure to inhibit phrenic nerve activity while delivering cardiac paces. Some embodiments allow the device to store posture, activity, time of day and the like whenever the pace-induced phrenic nerve activation are detected to determine the context when the unintended phrenic nerve activation is observed. According to some embodiments, the device is configured to use this contextual information to enable a phrenic nerve inhibition routine only during these contextual situations in which the pace-induced phrenic nerve activation previously occurred.

FIGS. 1A-1E illustrate various implantable device embodiments configured to stimulate the left ventricle and configured to inhibit phrenic nerve activity. The illustrated device is an implantable medical device 100 used to perform a cardiac tissue stimulation therapy, such as CRT or other pacing therapies, using leads represented by the dotted lines and electrodes represented by "X" fed into the right atrium, right ventricle, and coronary sinus of the heart. The lead 101 passing through the coronary sinus of the heart includes a left ventricular electrode 102, or electrodes, for use to stimulate the left ventricle at a stimulation site.

Figure 1B:
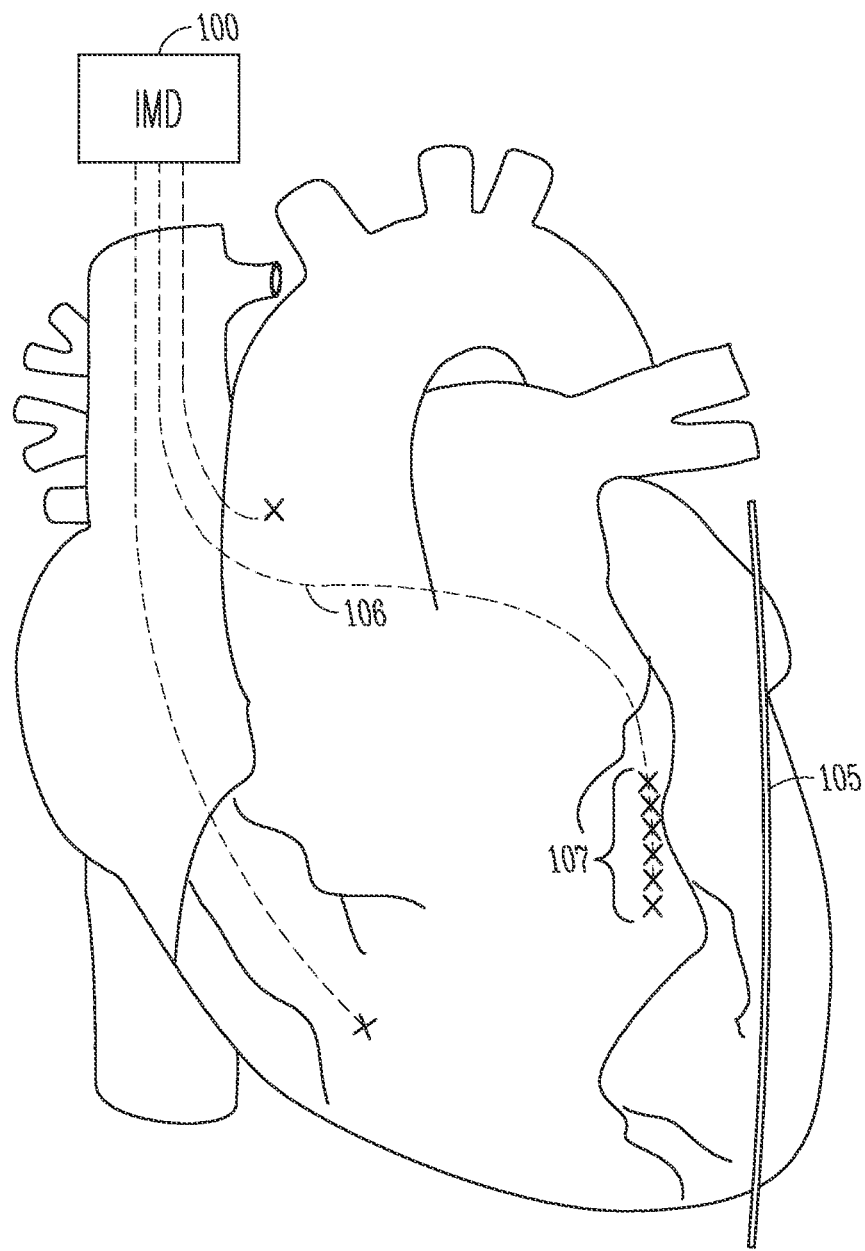
Figure 1C:
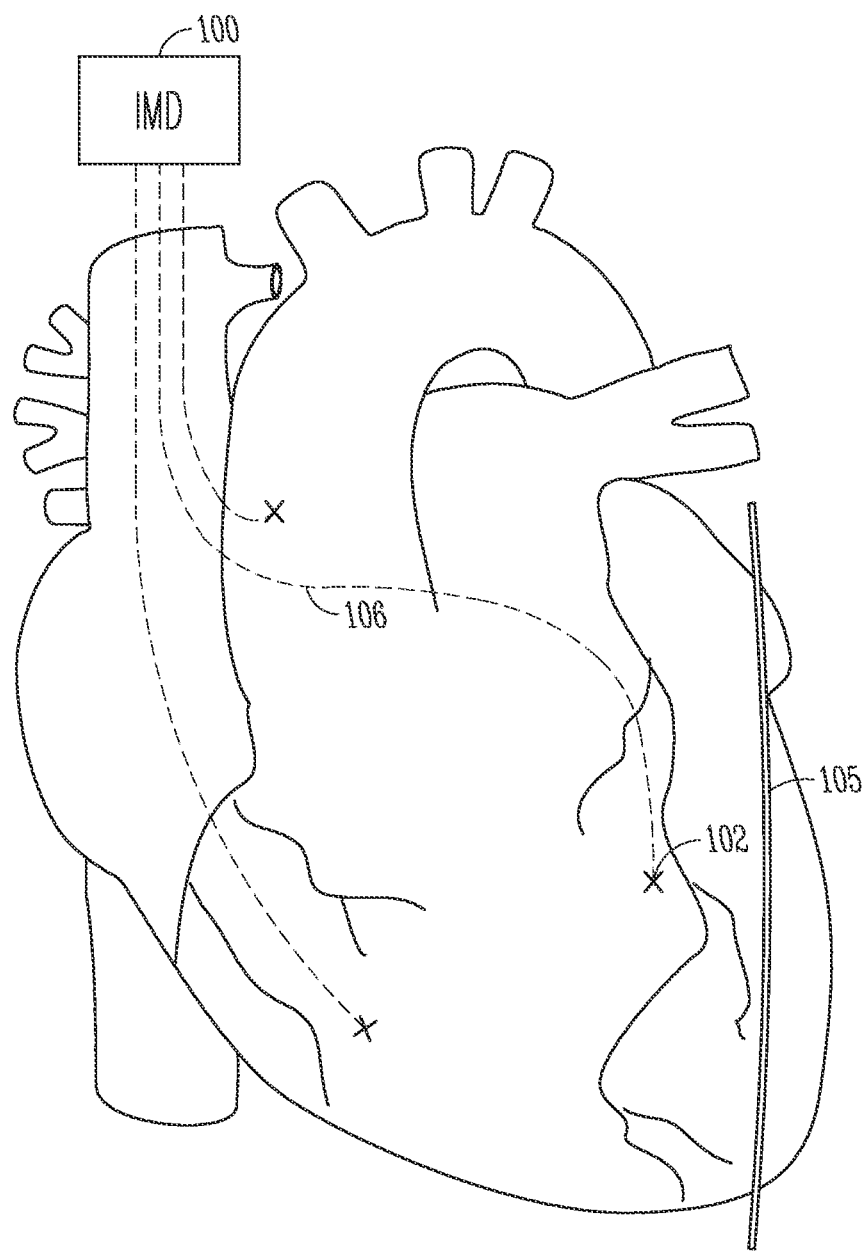
Figure 1D:
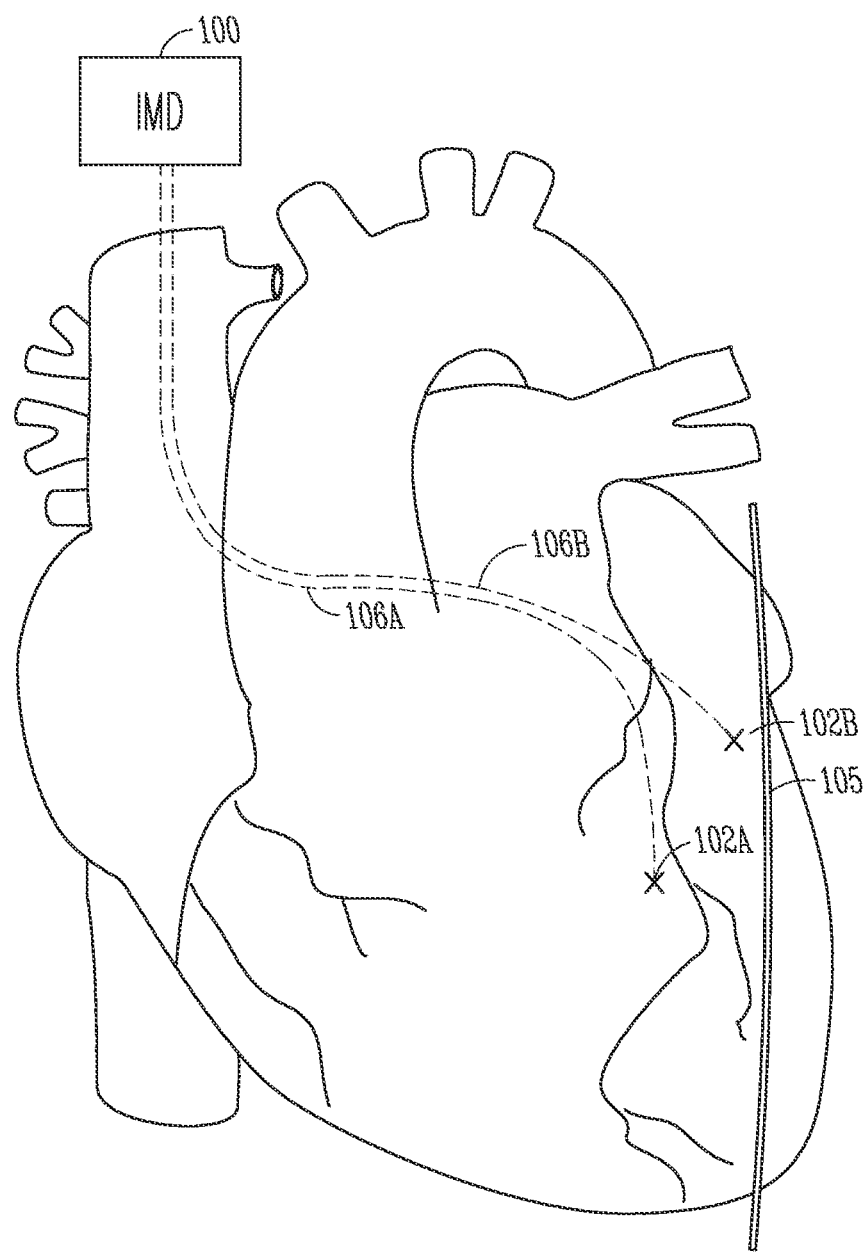

In FIG. 1A, the device has a phrenic nerve lead 103 with a nerve cuff electrode 104. The phrenic nerve lead 103 may be subcutaneously tunneled from the device 100 to the phrenic nerve 105, and the device is configured to use the phrenic nerve lead 103 and nerve cuff electrode 104 to inhibit the phrenic nerve 105. In some embodiments, more than one implantable device can be used, where one device provides the cardiac tissue stimulation therapy and another device provides the desired inhibition of the phrenic nerve. The inhibition signal prevents the left ventricle cardiac pace from capturing the left phrenic nerve that passes near the left ventricular stimulation site. In FIG. 1B, the device 100 has a left ventricular lead 106 with a plurality of electrodes 107 within a coronary sinus tributary to stimulate at least a first site and a second site. The device 100 is configured to use at least one of the electrodes 107 to stimulate the first site to deliver left ventricular paces, and is configured to use at least one other electrode to inhibit nerve traffic in the phrenic nerve 105. Various device embodiments perform an algorithm that assists the clinician with determining which of the electrodes to use to inhibit phrenic nerve activity and which of the electrodes to use for left ventricular pacing. According to some embodiments, the device is programmed to use sensors to detect unintended phrenic nerve activity or diaphragm contraction and to automatically choose electrodes from which to inhibit nerve activity. In FIG. 1C, the device 100 has a left ventricular lead 106 with an electrode 102, wherein the device use electrode 102 positioned with a coronary sinus tributary to both pace the left ventricle and to inhibit the phrenic nerve. Thus, the same electrode can be used for cardiac capture and phrenic nerve block, or different electrodes could be used where the different electrodes are either on the same or on different electrodes. Any electrode proximate to the phrenic nerve can be used to provide electrical blocking of the nerve during a cardiac pacing pulse. The electrical blocking of the nerve can be initiated before and/or during the delivery of the cardiac pacing pulse. In some embodiments, the electrical blocking signal for the phrenic nerve is terminated after the cardiac pacing pulse. Some embodiments terminate the electrical blocking during the cardiac pacing pulse, and some embodiments terminate the electrical blocking just prior to the cardiac pacing pulse. In FIG. 1D, the device 100 has a left ventricular leads 106A and B, each with at least one electrode 102A and B, wherein the device uses electrodes 102A and B to in a stimulation configuration to inhibit the phrenic nerve. The leads 106A and B are fed into different veins. Some embodiments use more than one left ventricular lead to inhibit the phrenic nerve. Some embodiments use a bifurcated lead to inhibit the phrenic nerve, where the ends of the bifurcated lead extend into the different veins. Some embodiments use other leads (e.g. an RV lead with an LV lead) to inhibit the phrenic nerve, and some embodiments use a can electrode to inhibit the phrenic nerve. Some embodiments use epicardial electrodes to inhibit the phrenic nerve.

According to various embodiments, a selective, nerve-blocking pulse waveform (sub-cardiac threshold) is delivered before and/or during pacing of the left ventricle. This pulse will prevent nerve capture during the pacing pulse and thereby prevent activation of the diaphragm. The electrical inhibition or block of the phrenic nerve can be achieved by: hyperpolarization of the nerve axons using a DC current pulse; depolarization of the nerve axons using a DC current pulse; and/or a high-frequency AC waveform (>1 KHz).

Figure 1E:
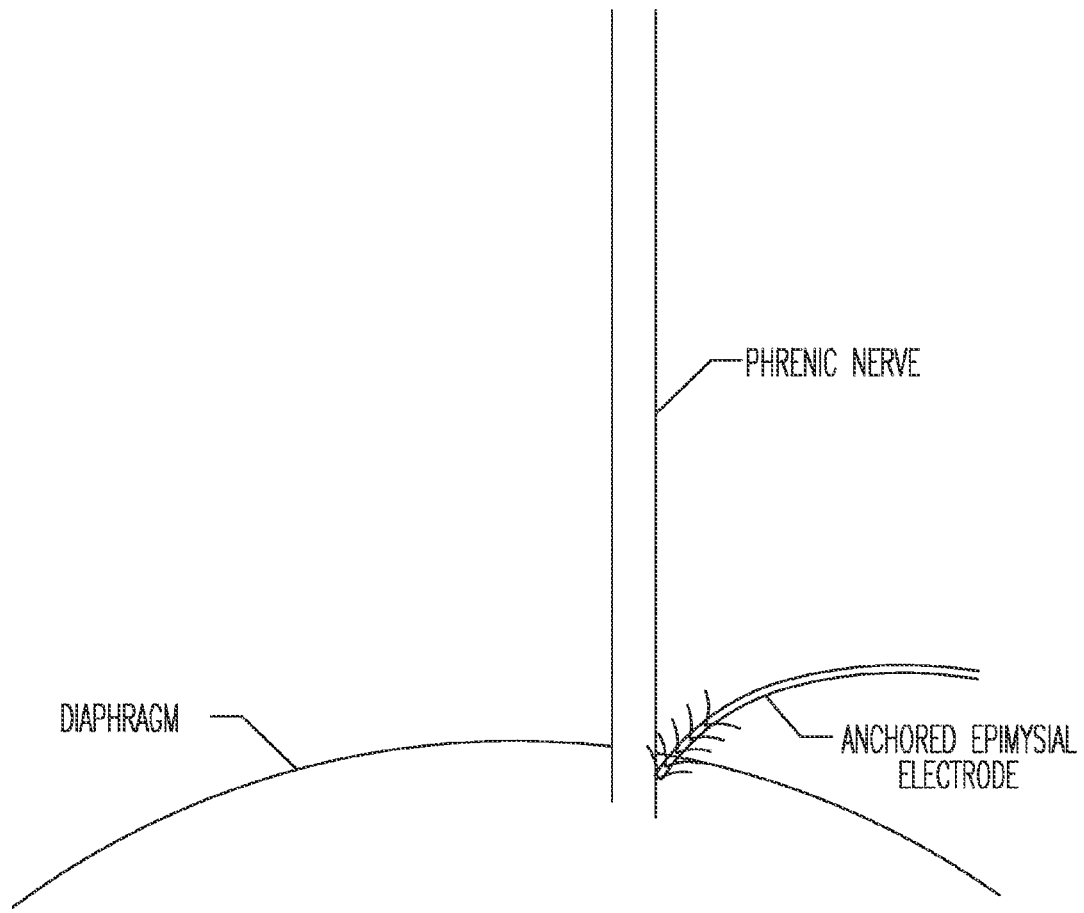

A number of electrode configurations can be used. The illustrations included herein are provided as examples, and are not intended to be an exhaustive listing of possible configurations. For example some embodiments use a percutaneous or laparoscopic approach to put an epimysial electrode in the diaphragm near the phrenic nerve or nerves or at other locations near the phrenic nerve(s). FIG. 1E generally illustrates placement of the epimysial electrode in the diaphragm near the phrenic nerve.

Figure 2:
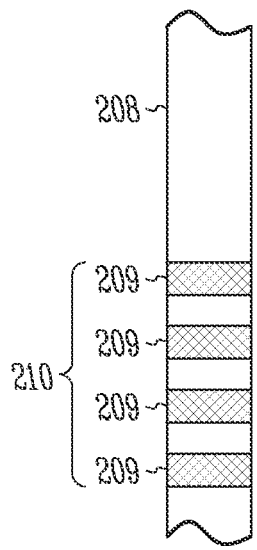
FIG. 2 illustrates an embodiment of a lead with annular stimulation electrodes that form an electrode region, according to various embodiments.
Figure 3:
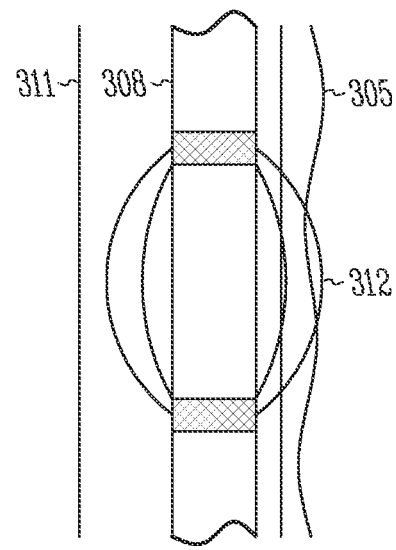
FIG. 3 illustrates a transluminal neural stimulation using electrodes within the lumen, according to various embodiments.
Figure 4A:
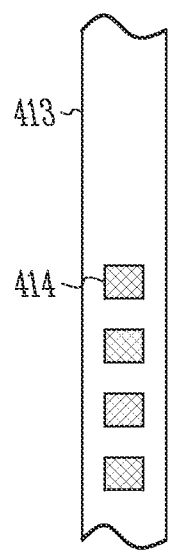
FIGS. 4A and 4B illustrate an embodiment of a lead with stimulation electrodes, where the illustrated electrodes do not circumscribe the lead.
Figure 4B:
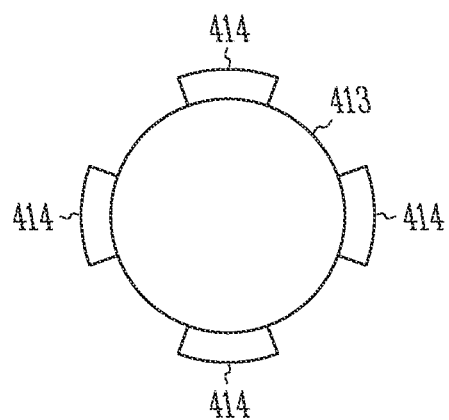

FIG. 2 illustrates an embodiment of a lead 208 with annular stimulation electrodes 209 that form an electrode region 210, according to various embodiments. Any one or combination of the annular stimulation electrodes can be used to deliver the neural stimulation. FIG. 3 illustrates a transluminal neural stimulation using electrodes within a lumen, according to various embodiments. The figure illustrates a lumen 311 (e.g. a tributary of the coronary sinus), a phrenic nerve 305 external to the lumen, and a lead 308 within the lumen. The neural stimulation generates an electrical field 312 between the electrodes that extends past the lumen wall to the nerve. FIGS. 4A and 4B illustrate an embodiment of a lead 413 with stimulation electrodes 414, where the illustrated electrodes do not circumscribe the lead. Thus, a subset of the illustrated electrodes can be selected to provide directional stimulation. For example, the lead may twist or rotate as it is fed into a coronary sinus tributary, and it may be desired to stimulate a phrenic nerve on one side of the lead without stimulating tissue on the other sides of the lead. A neural stimulation test routine can cycle through the available electrodes for use in delivering the neural stimulation to determine which electrodes are most appropriate to block the phrenic nerve.

There are several ways for delivering an electrical nerve block. In some embodiments, for example, DC current pulses can be applied to the nerve membrane within the electric field of the pulse. A DC pulse can hyperpolarize if its amplitude is below the resting membrane voltage or depolarize the membrane if its amplitude is above the resting membrane voltage but below the threshold required to generate an action potential. Both types of pulses are capable of inducing block by modifying the excitation properties of the ion channels within the nerve membrane. In another embodiment, for example, a high-frequency waveform e.g. on the order of 1 KHz or greater) is applied, which changes the excitable status of the nerve membrane under the stimulation field. Various embodiments block the phrenic nerve by stimulating through the closest electrode(s) to the nerve. Electrical block can be achieved using high frequency or constant DC pulses. For example, some embodiments deliver a high (frequency or amplitude) pulse that starts during the refractory period of the heart, avoiding capture of the myocardium and then ramps down to a low frequency or amplitude level during the pacing pulse, thus allowing cardiac response but maintaining phrenic nerve block.

Figure 5A:
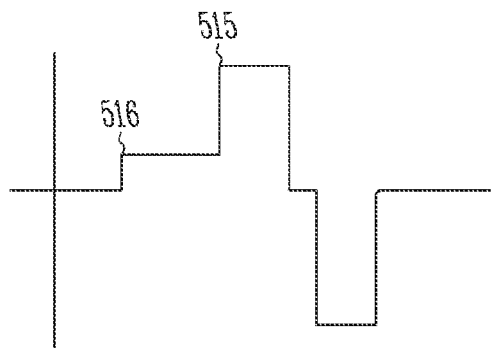
FIGS. 5A-5E illustrate various signals that provide cardiac pacing and phrenic nerve inhibition using the same electrode, according to various embodiments of the present subject matter.
Figure 5B:
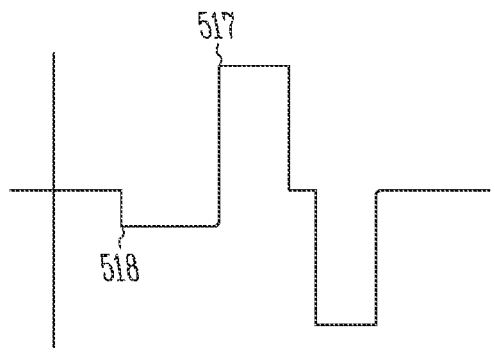
Figure 5C:
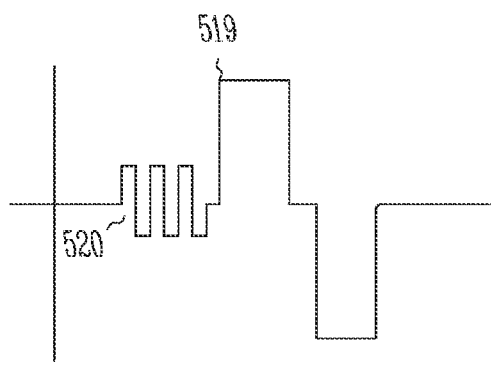
Figure 5D:
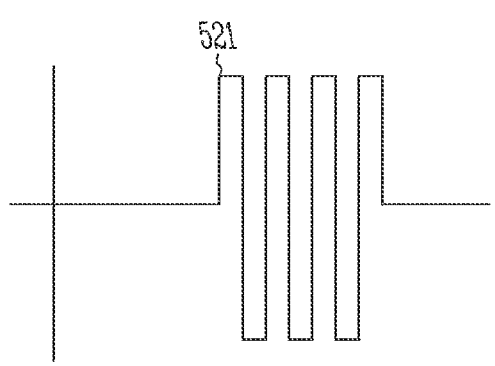
Figure 5E:
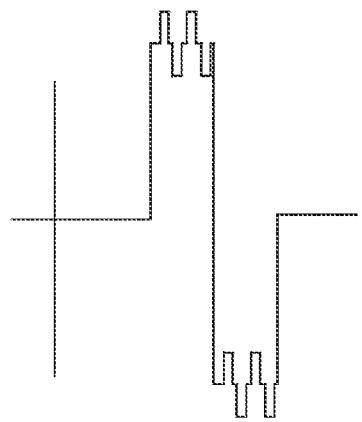

FIGS. 5A-5E illustrate various signals that provide cardiac pacing and phrenic nerve inhibition using the same electrode, according to various embodiments of the present subject matter. FIG. 5A illustrates a biphasic cardiac pace 515 preceded by an inhibition pulse 516 that provides a constant depolarizing DC pulse that blocks the nerve axons in anticipation of the cardiac pace. FIG. 5B illustrates a biphasic cardiac pace 517 preceded by a constant hyperpolarizing DC pulse 518 that blocks the nerve axons before the cardiac pacing pulse. FIG. 5C illustrates a biphasic cardiac pace 519 preceded by an inhibition signal 520 that includes a high-frequency waveform (e.g. on the order of 1 KHz or greater), which blocks the nerve axons in anticipation of the cardiac pacing pulse. FIG. 5D illustrates a signal 521 that delivers a cardiac pace and inhibits phrenic nerve activity simultaneously. The amplitude of the pace 521 is similar to the amplitude of the biphasic paces 515, 517 and 519, and the pulse frequency of the pulses within the pace is similar to high pulse frequency of the inhibition signal 520. FIG. 5E illustrates another signal that delivers a cardiac pace and inhibits phrenic nerve activity simultaneously. The signal illustrates a biphasic pulse for cardiac pacing, such as illustrated at 517 in FIG. B, with a high frequency signal for phrenic nerve inhibition superimposed on the biphasic pulse. FIGS. 5A-5E illustrate square waves. However, the present subject matter may use other waveforms, such as sinusoidal and triangular waveforms by way of example and not limitation.

Regardless of whether the inhibition pulse and the cardiac pace are delivered by the same or different pulses, the cardiac pace is delivered at a desired pacing time, and the nerve traffic is inhibited in the phrenic nerve at a desired nerve traffic inhibition time. The desired pace time is determined by the pacing algorithm, and the desired pace time is used to determine the desired nerve traffic inhibition time to appropriately inhibit or block phrenic nerve activity when the cardiac pace is delivered.

Respiration involves both voluntary and involuntary actions. Muscles used in respiration include the diaphragm, intercostal, and abdominal muscles. The intercostal muscles provide expiratory and inspiratory functions, the abdominal muscles have an expiratory function, and the diaphragm provides an inspiratory function. Phrenic nerve activity controls the diaphragm, and is primarily active during the inspiration phase of the respiratory cycle. There may be some residual phrenic nerve activity after the inspiration phase. Respiration is a complex process involving many physiologic responses. For example, phrenic nerve activity is inhibited by lung volume-related afferents. Additionally, the diaphragm is innervated by a left and a right phrenic nerve. If one of the phrenic nerves has been severed, the other phrenic nerve continues to cause the diaphragm to contract (inspiration) to provide breathing, albeit more labored than if both phrenic nerves are functional.

FIGS. 6A-6E illustrate a respiratory cycle, cardiac paces, inhibited left phrenic nerve activity corresponding to the cardiac paces, and diaphragm activity when the left phrenic nerve is inhibited for the cardiac pulses. These figures are illustrative in nature, and are not drawn to scale.

The respiratory signal is a physiologic signal indicative of respiratory activities. In various embodiments, the respiratory signal includes any physiology signal that is modulated by respiration. In one embodiment, the respiratory signal is a transthoracic impedance signal sensed by an implantable impedance sensor. In another embodiment, the respiratory signal is extracted from a blood pressure signal that is sensed by an implantable pressure sensor and includes a respiratory component. In another embodiment, the respiratory signal is sensed by an external sensor that senses a signal indicative of chest movement or lung volume. According to various embodiments, peaks of a respiratory signal are detected as respiratory fiducial points. Respiration fiducial points can be used, either with or without a delay interval, to time the delivery of the phrenic nerve inhibition. In various other embodiments, onset points of the inspiration phases, ending points of the expiration phases, or other threshold-crossing points are detected as the respiratory fiducial points.

Figure 6A:
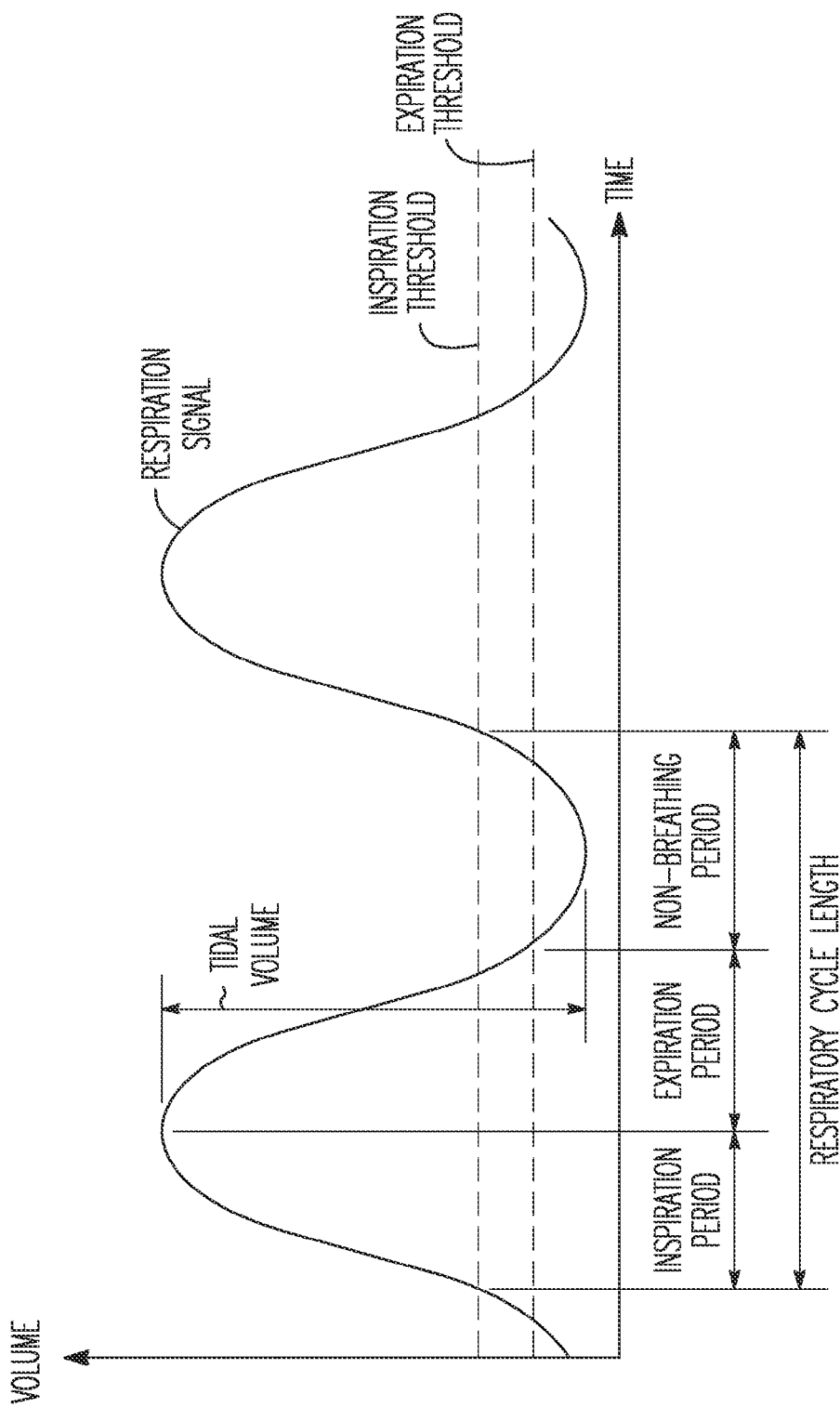
FIGS. 6A-6E illustrate a respiratory cycle, cardiac paces, inhibited left phrenic nerve activity corresponding to the cardiac paces, and diaphragm activity when the left phrenic nerve is inhibited for the cardiac pulses.

FIG. 6A illustrates a respiratory signal including respiratory cycle length, inspiration period, expiration period, non-breathing period, and tidal volume. By way of example, a respiratory variability can be determined using one or more of the parameters illustrated in the figure. The axes of the graph are volume and time, such that the signal represents the respiration volume over time. The inspiration period starts at the onset of the inspiration phase of a respiratory cycle, when the amplitude of the respiratory signal rises above an inspiration threshold, and ends at the onset of the expiration phase of the respiratory cycle, when the amplitude of the respiratory cycle peaks. The expiration period starts at the onset of the expiration phase and ends when the amplitude of the respiratory signal falls below an expiration threshold. The non-breathing period is the time interval between the end of the expiration phase and the beginning of the next inspiration phase. The tidal volume is the peak-to-peak amplitude of the respiratory signal. The respiratory rate can be determined from the cycle length: rate (br/min)=1/(cycle length) when the cycle length is provided in the units of minutes.

Figure 6B:
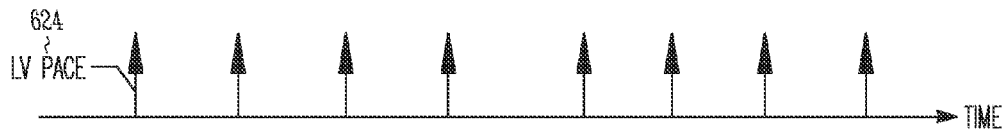

FIG. 6B illustrates a series of left ventricle (LV) paces 624. FIGS. 6A and 6B illustrate, by way of example and not limitation, about four cardiac cycles for each respiratory cycle. The phrenic nerve traffic is appropriately inhibited to prevent the LV paces from inducing phrenic nerve activity. By way of example and not limitation, some embodiments initiate nerve traffic inhibition a small time period before the anticipated LV pace 624 and for a duration extending to the end of the LV pace.

Figure 6C:
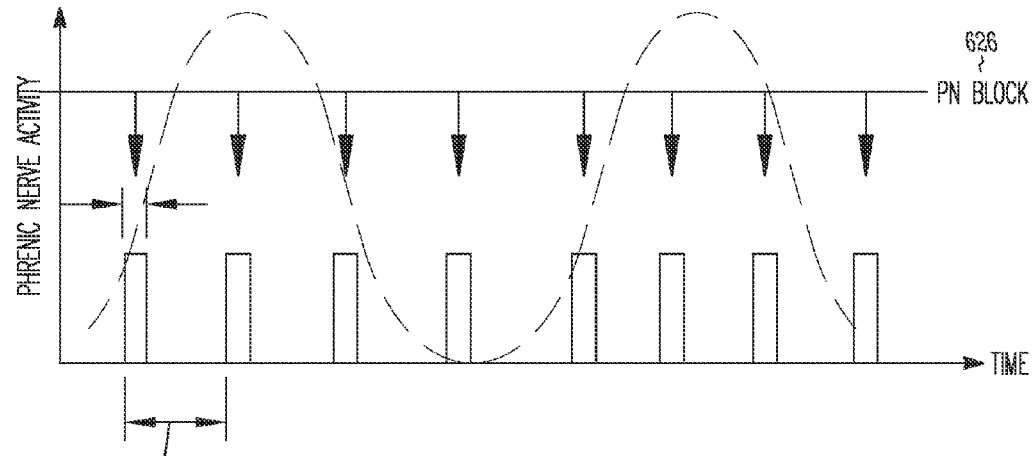

FIG. 6C illustrates the inspiration period 625, and further illustrates the phrenic nerve inhibition or block 626 such as may be delivered for at least some of the LV paces 624. The phrenic nerve activity predominately occurs during the inspiration period. Thus, FIG. 6C illustrates time periods of intrinsic phrenic nerve activity, and time periods when that intrinsic activity may be blocked according to some embodiments of the present subject matter. Phrenic nerve blocks outside of the inspiration period would not significantly affect respiration, as there is only some residual nerve traffic in other periods of the respiration cycle.

Figure 6D:
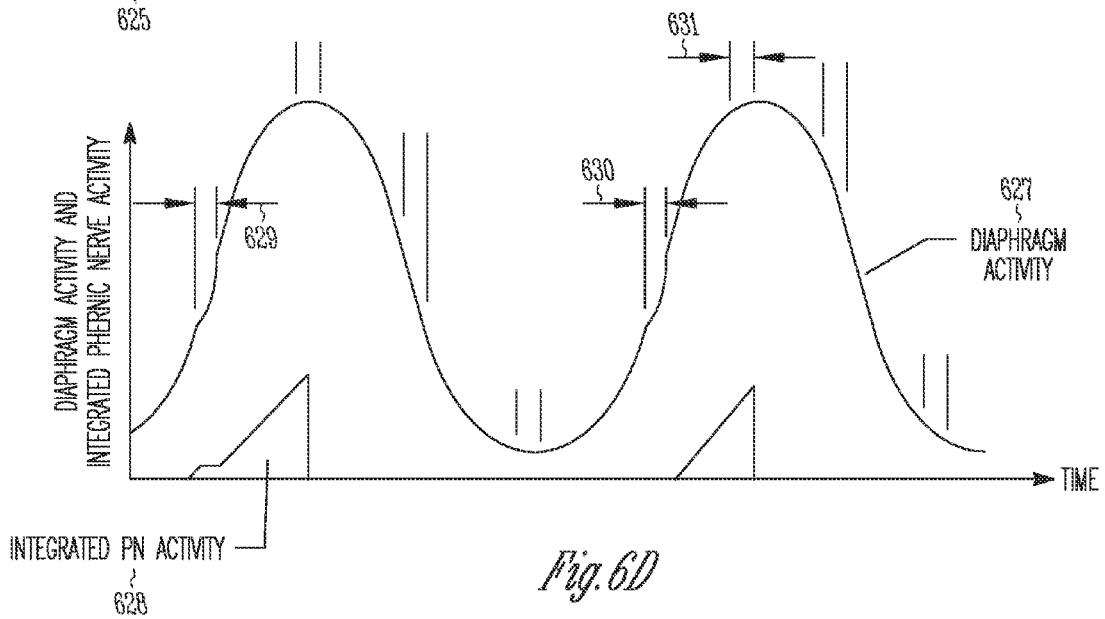
Figure 6E:

FIG. 6D illustrates diaphragm activity 627, which generally corresponds to the respiration cycle, and also illustrates the ramp-like integrated phrenic nerve activity 628 that occurs during respiration. FIG. 6E illustrates phrenic nerve activity for a respiratory cycle. The regions of the nerve blocking pulses that occur during inspiration are illustrated generally at 629, 630 and 631. FIG. 6C also illustrates other nerve blocking pulses throughout the respiratory cycle, and the times associated with these nerve blocking pulses are reflected in FIG. 6D. It is expected that the diaphragm activity will be affected slightly at regions 629 and 630. However, the time duration of these regions 629 and 630 is short in comparison to the over all respiratory cycle. Further, there is a cumulative recruitment of diaphragm muscle fibers during the inspiration process. Additionally, the other phrenic nerve (e.g. right phrenic nerve) continues to function to contract portions of the diaphragm that it innervates, as labored breathing can still occur if one of the phrenic nerves has been severed. Thus, it is expected that the diaphragm's contraction ability will not be affected during the phrenic nerve blocking pulse because the inhibition applied by the algorithm will be intermittent and of a short duration, and because the other phrenic nerve will remain active. The integrated phrenic nerve activity 628 is illustrated with a plateau corresponding to the time duration of the phrenic nerve blocking pulse region 629.

Blocking the phrenic nerve outside of the inspiration period for a respiration cycle may not significantly affect respiration, as these portions of the respiration cycle may not have significant intrinsic phrenic nerve traffic. Thus, a phrenic nerve blocking pulse would prevent cardiac paces from causing diaphragmatic stimulation during these portions of the respiration cycle without drastically affecting the respiration cycle. Further, some intrinsic phrenic nerve activity may be inhibited by the intrinsic physiology (e.g. by lung volume-related afferents) during portions of the respiratory cycle. During these portions of the respiratory cycle, it may or may not be necessary to use phrenic nerve blocking pulses to further inhibit the diaphragmatic stimulation caused by cardiac paces. Also, certain portions of the inspiration period will have very significant phrenic nerve activity, e.g. at the end of the inspiration phase during deep breathing. If the diaphragm is fully contracted at such a time in the respiratory cycle, then it may not be expected that a cardiac pace would cause diaphragmatic stimulation. In addition, there may be periods in the respiratory cycle during which the distance between the phrenic nerve and the cardiac pacing lead is increased such that the electric field produced by the cardiac pacing pulse is not strong enough to elicit a diaphragmatic response via the phrenic nerve. Changes in this distance could be a result of lung-volume-induced changes in the anatomical alignment of the organs in the mediastinum or of changes in body position. Based on these and other factors, only certain portions of the respiratory cycle may be susceptible to cardiac-pace-induced diaphragmatic stimulation. Some embodiments do not administer a blocking pulse (e.g. are not enabled) during certain phases of respiratory cycle (e.g. where unhampered diaphragm activation is desired, or where the intrinsic physiology makes it unlikely that the cardiac pace will stimulate the nerve). Thus, for certain patients, phrenic nerve blocking could be enabled with respiratory and other physiological sensing.

Figure 7:
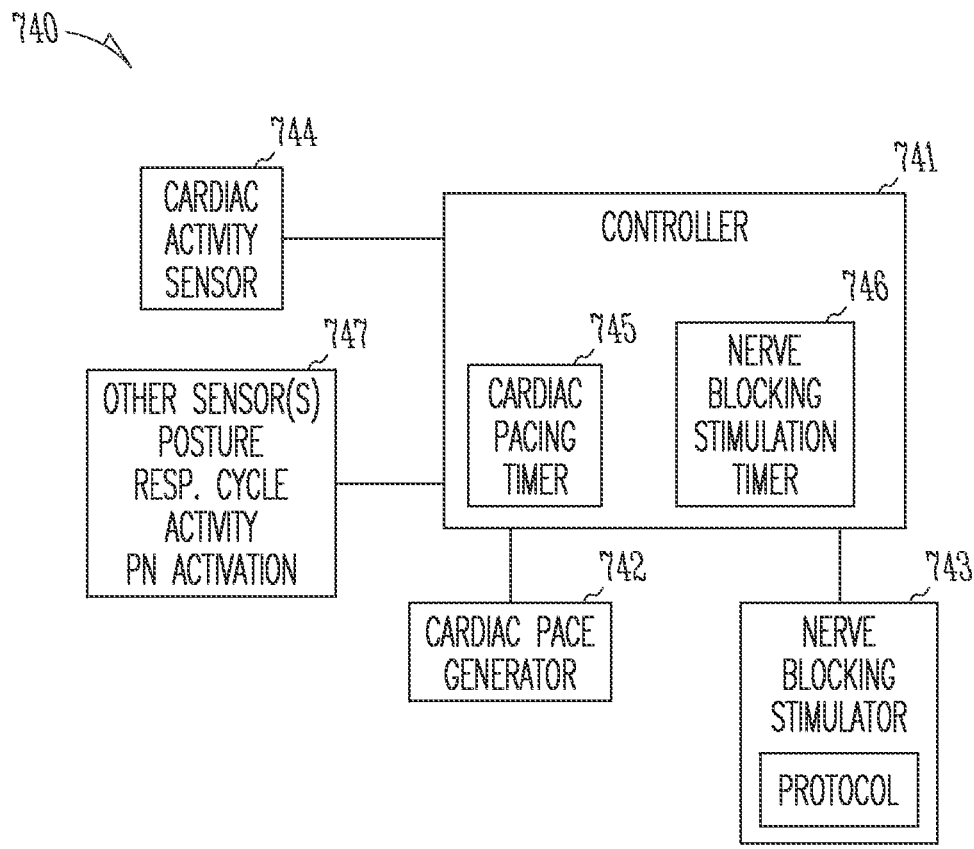
FIG. 7 illustrates a device embodiment.

FIG. 7 illustrates a device embodiment. The illustrated device 740 includes a controller 741, a cardiac pulse generator 742, a nerve blocking stimulator 743 and a cardiac activity sensor 744. The device is configured to implement a cardiac pacing algorithm. The controller 741 receives sensed cardiac activity from the cardiac activity sensor, and uses a cardiac pacing timer 745 to determine a pace time for delivering a cardiac pace and controls the cardiac pulse generator 742 to deliver the cardiac pace at the desired time. The controller 741 also includes a nerve blocking or inhibition stimulation timer 746 to determine an inhibition time for delivering phrenic nerve inhibition, and controls the nerve blocking stimulator 743 to generate the phrenic nerve inhibition at the inhibition time. The nerve blocking stimulator 743 is configured to deliver an appropriate electrical signal according to a protocol to effectively block or inhibit the phrenic nerve traffic. Protocol examples include a DC current pulse to hyperpolarize nerve axons in the phrenic nerve at the desired inhibition time, a depolarizing DC current pulse to modify the excitability of the nerve axons in the phrenic nerve at the desired inhibition time but without enough strength to generate propagated action potentials, and pulses at a pulse frequency greater than 1 KHz. In some embodiments, the controller is configured to implement a nerve traffic blocking algorithm only as need. For example, other sensor(s) 747 may be used to detect a pace-induced phrenic nerve activity, respiratory cycles, posture, activity, and the like.

Figure 8:
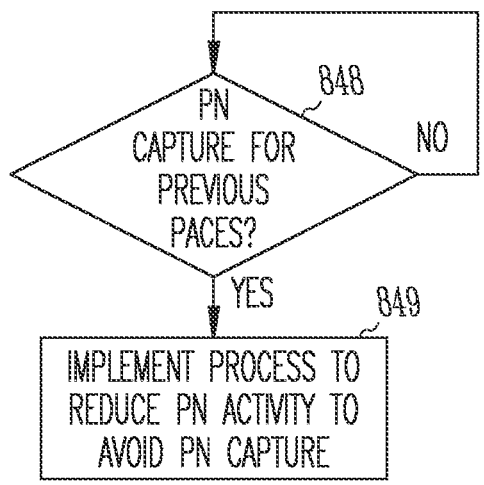
FIG. 8 illustrates an embodiment of a method that detects pace-induced phrenic nerve activation, and performs a phrenic nerve blocking routine to avoid the pace-induced phrenic nerve activation.

FIGS. 8-13 illustrate various methods embodiments. FIG. 8, for example, illustrates a method which detects pace-induced phrenic nerve activity, and performs a phrenic nerve blocking routine to avoid the pace-induced phrenic nerve activity. At 848, it is determined whether previous pace(s) capture the phrenic nerve. For example, diaphragm contraction from phrenic nerve activity may be detected by an accelerometer or acoustic sensor, and the timing of the sensed diaphragm contraction is compared to the timing of a cardiac pace to determine if the cardiac pace likely caused the phrenic nerve activity. Additional confidence can be obtained by comparing multiple diaphragm contractions to multiple paces. If it is determined that the pace is inducing unwanted phrenic nerve activity (PN capture), then a process is implemented to reduce phrenic nerve activity to avoid capture of the phrenic nerve 849. The device can be programmed to verify whether the phrenic nerve is still captured after a period of time or after a number of paces or after a change in a contextual event such as a change from lying down to standing up.

Figure 9:
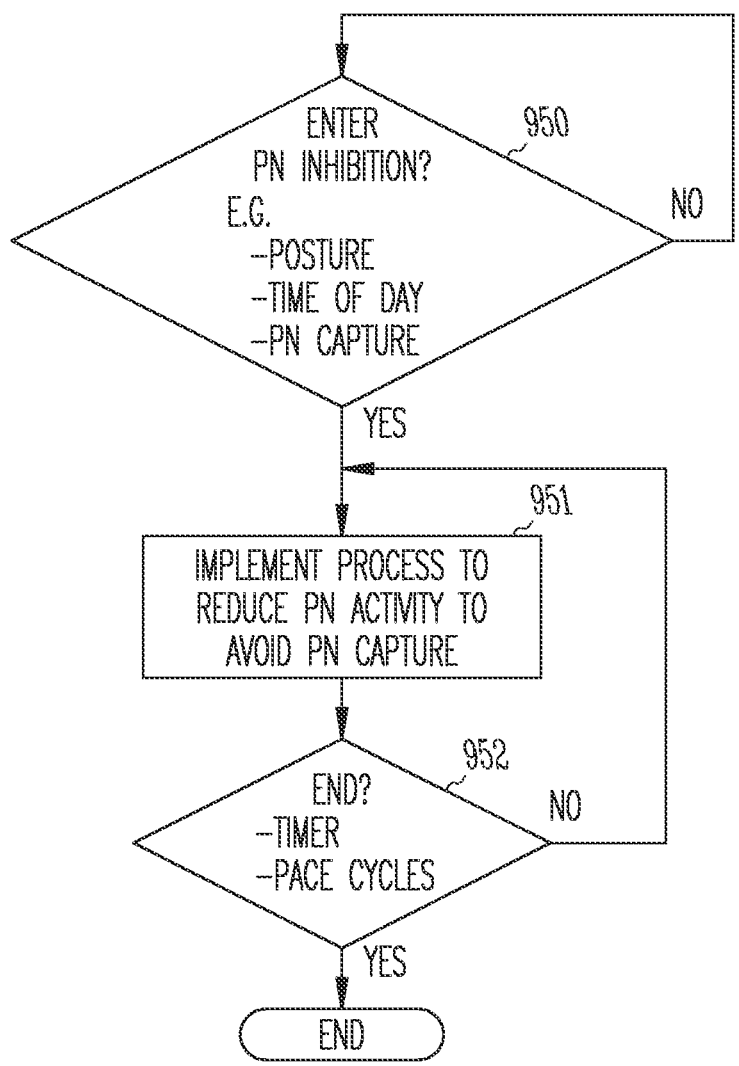
FIG. 9 illustrates various embodiments that determine when to implement and when to end a phrenic nerve inhibition process.

FIG. 9 illustrates various embodiments that determine when to implement and when to end a phrenic nerve inhibition process. At 950, it is determined whether to enable or otherwise implement a phrenic nerve traffic blocking or inhibition algorithm. For example, posture, time of day, and/or a detected capture of the phrenic nerve may be used to enable the process. At 951, the process to reduce phrenic nerve activity to avoid phrenic nerve capture is implemented. At 952, it is determined whether to end the process because the duration of the process extends to a particular period of time or a number of pace cycles, or because a contextual event (e.g. posture or activity) changed.

Figure 10:
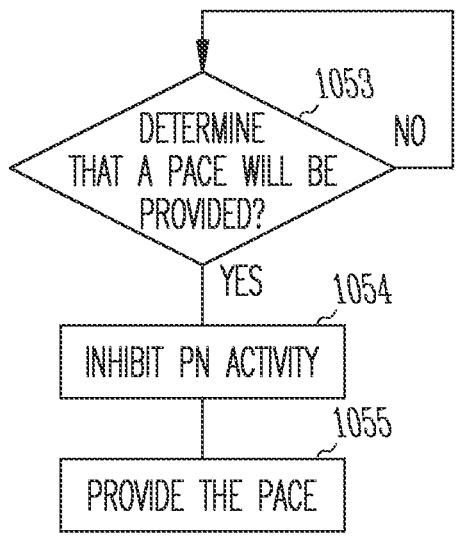
FIGS. 10 and 11 illustrate various embodiments for implementing a process to reduce phrenic nerve activity.
Figure 11:
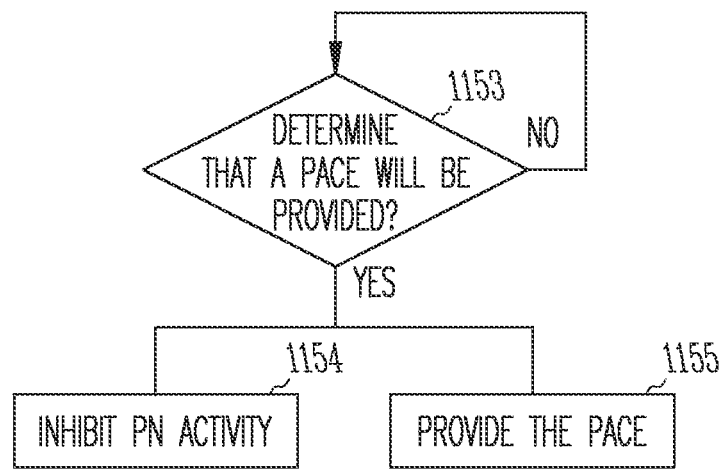

FIGS. 10 and 11 illustrate various embodiments for implementing a process to reduce phrenic nerve activity. A cardiac pacing algorithm, for example, determines that a pace will be provided and when the pace will be provided 1053 and 1153. Rather than being integrated with a CRM system, some embodiments may be implemented as a stand alone nerve traffic inhibitor. Such embodiments need not determine when the pace will be provided, but rather may just receive a desired cardiac pace time from the CRM system. Some embodiments inhibit phrenic nerve activity 1054 before the pace is provided 1055 as illustrated in FIG. 10 and some embodiments inhibit phrenic nerve activity 1154 as the pace is being provided 1155 as illustrated in FIG. 11.

Figure 12:
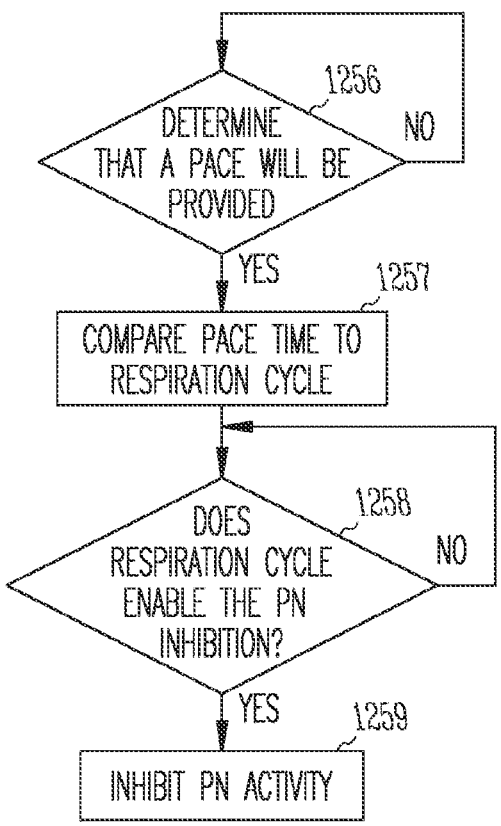
FIG. 12 illustrates an embodiment of a method for using respiration to enable phrenic nerve traffic inhibition.

FIG. 12 illustrates an embodiment of a method for using respiration to enable phrenic nerve traffic inhibition. At 1256, it is determined whether a cardiac pace will be provided and a cardiac pace time for delivering the pace. At 1257, the determined pace time is compared to the respiration cycle, and this comparison is used to determine whether the respiration cycle enables the inhibition of the phrenic nerve 1258. If the pace time is at an appropriate time in the respiratory cycle, then the phrenic nerve activity is inhibited 1259.

Figure 13:
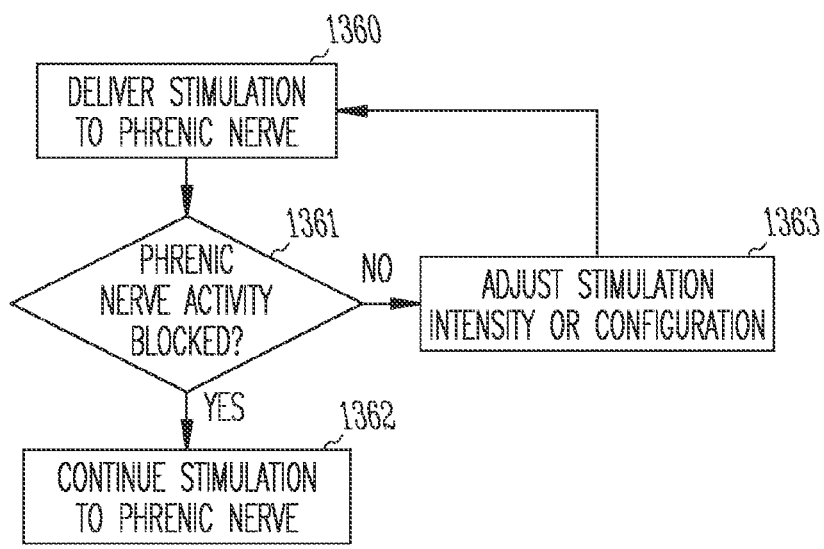
FIG. 13 illustrates an embodiment that titrates the intensity or configuration of the inhibition stimulation to achieve the desired phrenic nerve inhibition.

Various embodiments titrate the blocking stimulation, as the threshold to block phrenic nerve activity may change with time (due to reverse remodeling for example), position, and the like. Examples of adjusting stimulation can be found in U.S. Pat. No. 6,772,008 entitled Method and Apparatus for Avoidance of Phrenic Nerve Stimulation During Cardiac Pacing", U.S. Pat. No. 7,299,093 entitled "Method and Apparatus for Avoidance of Phrenic Nerve Stimulation During Cardiac Pacing", U.S. Pat. No. 7,392,086 entitled "Implantable Cardiac Device and Method for Reduced Phrenic Nerve Stimulation", and Gurevitz et al. entitled "Programmable Multiple Pacing Configurations Help to Overcome High Left Ventricular Pacing Thresholds and Avoid Phrenic Nerve Stimulation", Pace, Vol. 28, 1255 (2005). These references (U.S. Pat. Nos. 6,772,008, 7,299,093, 7,392,086 and Gurevitz et al.) are incorporated herein by reference in their entirety. FIG. 13 illustrates an embodiment that titrates the intensity or configuration of the inhibition stimulation to achieve the desired phrenic nerve inhibition. At 1360, stimulation is delivered to inhibit phrenic nerve traffic. If phrenic nerve activity is blocked or inhibited, at 1361, the stimulation to inhibit phrenic nerve traffic continues at 1362. If phrenic nerve activity is not blocked or inhibited, the stimulation intensity (e.g. amplitude) or stimulation configuration between or among electrodes are adjusted at 1363. It can be determined whether the phrenic nerve activity is sufficiently blocked by determining if pace-induced phrenic nerve activity is detected when the inhibition stimulation is being delivered.

Figure 14:
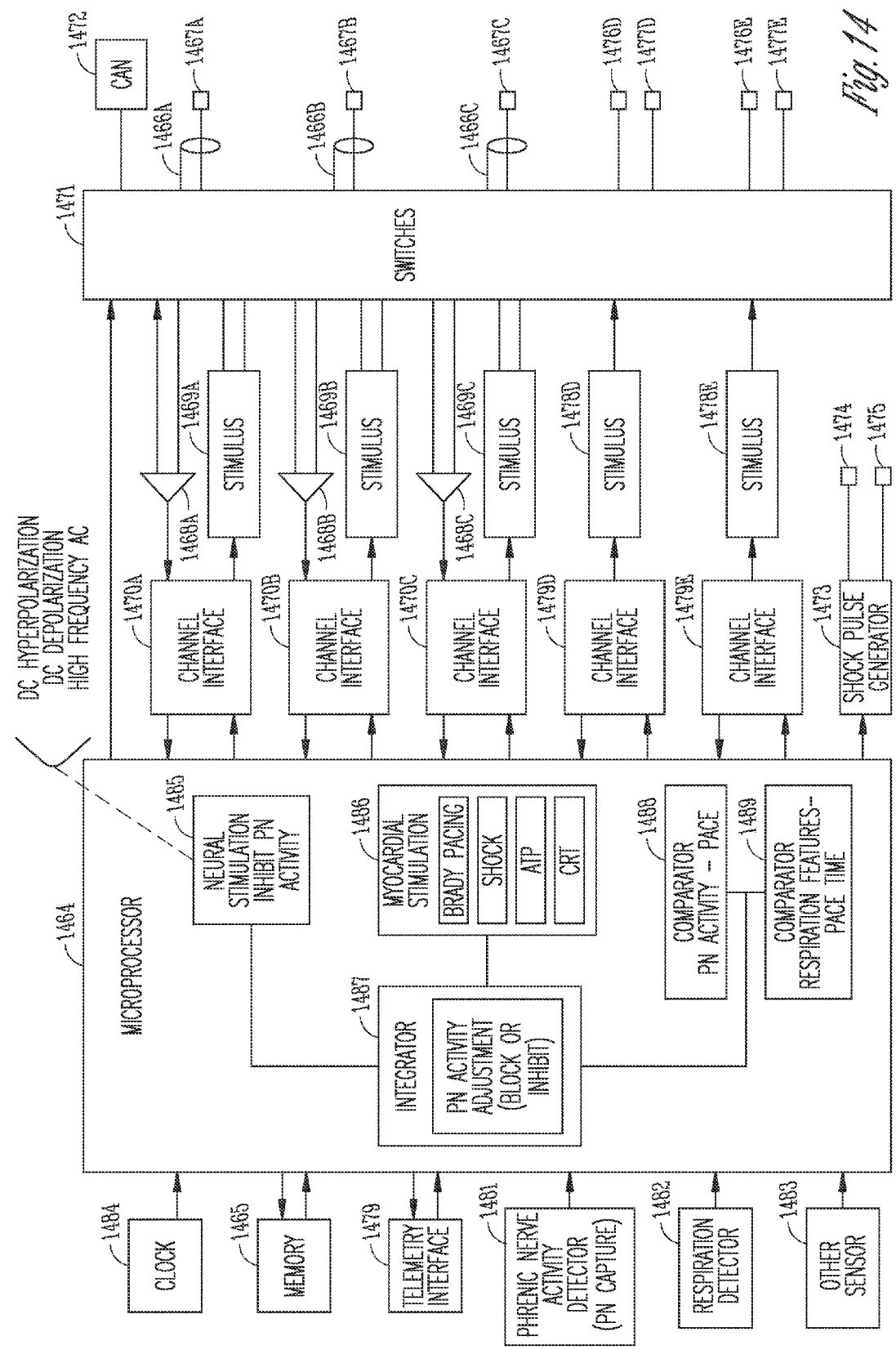
FIG. 14 illustrates a system diagram of an embodiment of a microprocessor-based implantable device.

FIG. 14 illustrates a system diagram of an embodiment of a microprocessor-based implantable device. The controller of the device is a microprocessor 1464 which communicates with a memory 1465 via a bidirectional data bus. The controller could be implemented by other types of logic circuitry (e.g., discrete components or programmable logic arrays) using a state machine type of design. As used herein, the term "circuitry" should be taken to refer to either discrete logic circuitry or to the programming of a microprocessor. Shown in the figure are three examples of sensing and pacing channels designated "A" through "C" comprising bipolar leads with ring electrodes 1466A-C and tip electrodes 1467A-C, sensing amplifiers 1468A-C, pulse generators 1469A-C, and channel interfaces 1470A-C. In some embodiments, the leads of the cardiac stimulation electrodes are replaced by wireless links. Each channel thus includes a pacing channel made up of the pulse generator connected to the electrode and a sensing channel made up of the sense amplifier connected to the electrode. The channel interfaces communicate bidirectionally with the microprocessor, and each interface may include analog-to-digital converters for digitizing sensing signal inputs from the sensing amplifiers and registers that can be written to by the microprocessor in order to output pacing pulses, change the pacing pulse amplitude, and adjust the gain and threshold values for the sensing amplifiers. The sensing circuitry of the pacemaker detects intrinsic chamber activity, termed either an atrial sense or ventricular sense, when an electrogram signal (i.e., a voltage sensed by an electrode representing cardiac electrical activity) generated by a particular channel exceeds a specified detection threshold. Pacing algorithms used in particular pacing modes employ such senses to trigger or inhibit pacing. The intrinsic atrial and/or ventricular rates can be measured by measuring the time intervals between atrial and ventricular senses, respectively, and used to detect atrial and ventricular tachyarrhythmias.

The electrodes of each bipolar lead are connected via conductors within the lead to a switching network 1471 controlled by the microprocessor. The switching network is used to switch the electrodes to the input of a sense amplifier in order to detect intrinsic cardiac activity and to the output of a pulse generator in order to deliver a pacing pulse. The switching network also enables the device to sense or pace either in a bipolar mode using both the ring and tip electrodes of a lead or in an extended bipolar or in a unipolar mode using only one of the electrodes of the lead with the device housing (can) 1472 or an electrode on another lead serving as a ground electrode. A shock pulse generator 1473 is also interfaced to the controller for delivering a defibrillation shock via a pair of shock electrodes 1474 and 1475 to the atria or ventricles upon detection of a shockable tachyarrhythmia. A can electrode may be used to deliver shocks.

Neural stimulation channels, identified as channels D and E, are incorporated into the device, where one channel includes a bipolar lead with a first electrode 1476D and a second electrode 1477D, a pulse generator 1478D, and a channel interface 1479D, and the other channel includes a bipolar lead with a first electrode 1476E and a second electrode 1477E, a pulse generator 1478E, and a channel interface 1479E. Other embodiments may use unipolar leads in which case the neural stimulation pulses are referenced to the can or another electrode. The pulse generator for each channel outputs a train of neural stimulation pulses which may be varied by the controller as to amplitude, frequency, duty-cycle, and the like. In this embodiment, each of the neural stimulation channels uses a lead which can be intravascularly disposed near an appropriate neural target. Other types of leads and/or electrodes may also be employed. A nerve cuff electrode may be used in place of an intravascularly disposed electrode to provide neural stimulation. In some embodiments, the leads of the neural stimulation electrodes are replaced by wireless links. The figure illustrates a telemetry interface 1479 connected to the microprocessor, which can be used to communicate with an external device.

Various embodiments include one or more of the following: a pace-induced phrenic nerve activity detector 1481 to detect phrenic nerve capture, a respiration detector 1482 and/or other sensor(s) 1483 such as to provide contextual information like activity and posture. According to various embodiments, the phrenic nerve activity detector may include, but is not limited to, an accelerometer, an acoustic sensor, a respiration sensor, impedance sensors, neural sensor on the phrenic nerve, or electrodes to sense electromyogram signals indicative of diaphragm contraction. Various embodiments use more than one detector to provide a composite signal that indicates phrenic nerve capture. The illustrated embodiment also includes a clock 1484.

The illustrated microprocessor 1464 is capable of performing phrenic nerve traffic inhibition routines 1485, and cardiac tissue (e.g. myocardial) stimulation routines 1486. Examples of phrenic nerve traffic inhibition routines include hyperpolarization the nerve axons using a DC current pulse; depolarization of the nerve axons using a DC current pulse; and/or a high-frequency AC waveform (>1 KHz). Examples of myocardial therapy routines include bradycardia pacing therapies, anti-tachycardia shock therapies such as cardioversion or defibrillation therapies, anti-tachycardia pacing therapies (ATP), and cardiac resynchronization therapies (CRT). The illustrated controller is able to perform routines 1487 to integrate myocardial stimulation with phrenic nerve traffic inhibition to avoid pace-induced phrenic nerve activity. The illustrated controller 1464 also includes a comparator 1488 to compare time when phrenic nerve activity is detected to a pace time to determine that the phrenic nerve activity is attributed to the pace. The controller 1464 also includes a comparator 1489 to compare respiration features to the pace time, and enable the phrenic nerve traffic inhibition if the pace time occurs during a programmed time of the respiration.

The neural stimulation to inhibit phrenic nerve activity and cardiac rhythm management functions may be integrated in the same device, as generally illustrated in FIG. 14 or may be separated into functions performed by separate devices.

One of ordinary skill in the art will understand that, the modules and other circuitry shown and described herein can be implemented using software, hardware, firmware and combinations thereof.

The methods illustrated in this disclosure are not intended to be exclusive of other methods within the scope of the present subject matter. Those of ordinary skill in the art will understand, upon reading and comprehending this disclosure, other methods within the scope of the present subject matter. The above-identified embodiments, and portions of the illustrated embodiments, are not necessarily mutually exclusive. These embodiments, or portions thereof, can be combined. In various embodiments, the methods are implemented using a sequence of instructions which, when executed by one or more processors, cause the processor(s) to perform the respective method. In various embodiments, the methods are implemented as a set of instructions contained on a computer-accessible medium such as a magnetic medium, an electronic medium, or an optical medium.

The above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A method for avoiding unwanted stimulation of a phrenic nerve during cardiac pacing, comprising:
   receiving a desired pace time for delivering a cardiac pace;
   determining a desired nerve traffic inhibition time to inhibit nerve traffic in the phrenic nerve, wherein determining the desired nerve traffic inhibition time includes using the desired pace time to determine the desired nerve traffic inhibition time; and
   inhibiting nerve traffic in the phrenic nerve at the desired nerve traffic inhibition time by delivering an electrical waveform to the phrenic nerve that modifies excitability of nerve axons in the phrenic nerve to inhibit nerve traffic in the phrenic nerve.

2. The method of claim 1, wherein inhibiting nerve traffic includes:
   delivering a DC current pulse to hyperpolarize nerve axons in the phrenic nerve at the desired inhibition time; or
   delivering a depolarizing DC current pulse to modify the excitability of nerve axons in the phrenic nerve at the desired inhibition time but without enough strength to generate propagated action potentials; or
   delivering pulses at a pulse frequency where the frequency is effectively high to modify the excitability of the nerve axons in the phrenic nerve at the desired inhibition time.

3. The method of claim 1, wherein inhibiting nerve traffic includes using at least one electrode in a coronary sinus tributary to inhibit nerve traffic in the phrenic nerve.

4. The method of claim 1, further comprising detecting pace-induced phrenic nerve activity, and wherein inhibiting nerve traffic includes implementing a process, in response to detecting the pace-induced phrenic nerve activity, to inhibit nerve traffic in the phrenic nerve.

5. The method of claim 1, further comprising detecting a respiration cycle, wherein inhibiting nerve traffic includes implementing a process to inhibit nerve traffic only for a portion of the detected respiration cycle.

6. A method for pacing a heart and avoiding unwanted stimulation of a phrenic nerve during cardiac pacing, comprising:
   determining a desired pacing time for delivering a cardiac pace;
   determining a desired nerve traffic inhibition time to inhibit nerve traffic in the phrenic nerve, wherein determining the desired nerve traffic inhibition time includes using the desired pace time to determine the desired nerve traffic inhibition time; and
   delivering the cardiac pace at the desired pacing time and inhibiting nerve traffic in the phrenic nerve at the desired nerve traffic inhibition time by delivering an electrical waveform to the phrenic nerve that modifies excitability of nerve axons in the phrenic nerve to inhibit nerve traffic in the phrenic nerve.

7. The method of claim 6, wherein:
   delivering the cardiac pace includes delivering the cardiac pace to a left ventricle of the heart; and
   inhibiting nerve traffic in the phrenic nerve includes inhibiting nerve traffic in a left phrenic nerve.

8. The method of claim 7, further comprising delivering cardiac resynchronization therapy (CRT), wherein delivering the CRT includes delivering the cardiac pace to a left ventricle of the heart.

9. The method of claim 7, further comprising using a common lead within a coronary sinus tributary to deliver the cardiac pace to the left ventricle and to inhibit nerve traffic in the left phrenic nerve.

10. The method of claim 6, wherein the desired nerve traffic inhibition time is initiated before or during the desired pace time.

11. A method for avoiding unwanted stimulation of a phrenic nerve during cardiac pacing, comprising:
    determining a desired nerve traffic inhibition time to inhibit nerve traffic in the phrenic nerve, wherein determining the desired nerve traffic inhibition time includes using a desired pace time for the cardiac pacing to determine the desired nerve traffic inhibition time; and
    inhibiting nerve traffic in the phrenic nerve at the desired nerve traffic inhibition time by delivering an electrical waveform to the phrenic nerve that modifies excitability of nerve axons in the phrenic nerve to inhibit nerve traffic in the phrenic nerve.

12. The method of claim 11, wherein delivering the electrical waveform to the phrenic nerve includes delivering a hyperpolarizing DC current pulse.

13. The method of claim 11, wherein delivering the electrical waveform to the phrenic nerve includes delivering a depolarizing DC current pulse.

14. The method of claim 11, wherein delivering the electrical waveform to the phrenic nerve includes delivering pulses at a frequency effectively high to modify the excitability of the nerve axons in the phrenic nerve at the desired inhibition time.

15. The method of claim 11, wherein inhibiting nerve traffic includes using at least one electrode in a coronary sinus tributary to inhibit nerve traffic in the phrenic nerve.

16. The method of claim 11, further comprising detecting pace-induced phrenic nerve activity, and wherein inhibiting nerve traffic includes implementing a process, in response to detecting the pace-induced phrenic nerve activity, to inhibit nerve traffic in the phrenic nerve.

17. The method of claim 11, further comprising detecting a respiration cycle, wherein inhibiting nerve traffic includes implementing a process to inhibit nerve traffic only for a portion of the detected respiration cycle.

18. The method of claim 11, further comprising determining the desired pacing time for delivering a cardiac pace, and delivering the cardiac pace at the desired pacing time.

19. The method of claim 11, further comprising a physiological sensor or a clock to detect a contextual event, wherein inhibiting nerve traffic in the phrenic nerve at the desired nerve traffic inhibition time includes enabling an ability to inhibit nerve traffic in the phrenic nerve for a time period after the contextual event.

20. The method of claim 11, further comprising detecting a respiration cycle, and using the detected respiration cycle to determine the desired nerve traffic inhibition time.

* * * * *